United States Patent
Trachtenberg (10) Patent No.: US 11,273,258 B2
(45) Date of Patent: Mar. 15, 2022

(54) INFUSION SET WITH LEAKAGE INDICATOR

(71) Applicant: Becton, Dickinson and Company, Franklin Lakes, NJ (US)

(72) Inventor: Matthew Trachtenberg, Hoboken, NJ (US)

(73) Assignee: Becton, Dickinson and Company

( * ) Notice: Subject to any disclaimer, the term of this patent is extended or adjusted under 35 U.S.C. 154(b) by 324 days.

(21) Appl. No.: 16/603,793

(22) PCT Filed: Apr. 19, 2018

(86) PCT No.: PCT/US2018/028337
§ 371 (c)(1),
(2) Date: Oct. 8, 2019

(87) PCT Pub. No.: WO2018/195298
PCT Pub. Date: Oct. 25, 2018

(65) Prior Publication Data
US 2021/0093779 A1   Apr. 1, 2021

Related U.S. Application Data

(60) Provisional application No. 62/488,002, filed on Apr. 20, 2017.

(51) Int. Cl.
*A61M 5/168* (2006.01)
*A61M 5/142* (2006.01)

(52) U.S. Cl.
CPC .... *A61M 5/16831* (2013.01); *A61M 5/14248* (2013.01); *A61M 2205/15* (2013.01); *A61M 2205/584* (2013.01)

(58) Field of Classification Search
CPC ...... A61M 5/16831; A61M 2005/1586; A61M 2005/1587; A61M 2005/1588; A61M 2205/15
See application file for complete search history.

(56) References Cited

U.S. PATENT DOCUMENTS 6,461,329 B1 * 10/2002 Van Antwerp .... A61M 5/16836
604/111
9,750,876 B2 * 9/2017 Nie .................... A61M 5/16831
(Continued)

FOREIGN PATENT DOCUMENTS

| EP | 1 263 488 A2 | 12/2002 |
| WO | 01/68163 A2 | 9/2001 |
| WO | 01/68163 A3 | 9/2001 |

OTHER PUBLICATIONS

Extended European Search Report dated Dec. 16, 2020, which issued in the corresponding European Patent Application No. 18787406.0.

(Continued)

*Primary Examiner* — Laura A Bouchelle
(74) *Attorney, Agent, or Firm* — Dickinson Wright PLLC (57) ABSTRACT

A delivery device is provided for introducing a fluid to a patient. The delivery device has a base with a bottom face for attaching to the skin of the patient, and a cannula extending from the bottom face for penetrating the skin of the patient. A fluid supply conduit has a first lumen connected to the cannula for supplying the fluid to the cannula, where the fluid contains an active agent and stabilizing agent. The conduit has a second lumen with an open end for capturing leakage of the fluid from the infusion site and carrying the fluid away from the infusion site. The second lumen has a leak detector containing a color changing in an amount to react with the stabilizing agent and produce a visual indication to the patient through the conduit. The leak detector is spaced from the infusion site and oriented in a location visible by the patient through the conduit.

22 Claims, 4 Drawing Sheets

(56) References Cited

U.S. PATENT DOCUMENTS

| | | |
|---|---|---|
| 2003/0069548 A1 | 4/2003 | Connelly et al. |
| 2004/0054338 A1 | 3/2004 | Bybordi et al. |
| 2006/0253085 A1 | 11/2006 | Geismar et al. |
| 2008/0195060 A1 | 8/2008 | Roger et al. |
| 2012/0143155 A1 | 6/2012 | Edvardsen et al. |
| 2012/0203198 A1 | 8/2012 | Searle et al. |
| 2014/0100522 A1 | 4/2014 | Nie et al. |
| 2015/0283321 A1 | 10/2015 | Dang et al. |

OTHER PUBLICATIONS

International Search Report dated Jul. 3, 2018, which issued in the corresponding PCT Patent Application No. PCT/US2018/028337.

* cited by examiner

INFUSION SET WITH LEAKAGE INDICATOR

This application claims priority to U.S. provisional patent application Ser. No. 62/488,002, filed on Apr. 20, 2017, which is hereby incorporated by reference in its entirety.

FIELD OF THE INVENTION

The present invention is directed to an infusion set with a leakage indicator for detecting leakage at an infusion site. The leakage indicator provides a visible indication to the patient that leakage is occurring or has occurred to enable the patient to correct the leakage.

BACKGROUND OF THE INVENTION

For patients with diabetes, there are two principal modes of daily insulin therapy. The first mode includes syringes and insulin pens. These devices are simple to use and are relatively low in cost, but they require a needle stick at each injection, typically three to four times per day. The second mode includes insulin infusion therapy, which utilizes an insulin pump. Infusion pumps, although more complex and expensive than syringes and pens, offer the advantages of continuous infusion of insulin via an infusion cannula, precision dosing, and programmable delivery schedules.

The use of an infusion pump requires the use of a disposable component, typically referred to as an infusion set, line set, extension set or pump set, which conveys the insulin from a reservoir within the pump into the skin of the user. An infusion set typically consists of a pump connector, a length of tubing, and a hub or base from which an infusion cannula (i.e., an infusion needle or a flexible catheter) extends. The hub or base has an adhesive to retain the base on the skin surface during use, and which may be applied to the skin manually or with the aid of a manual or automatic insertion device. In most cases, a detachable fluid connector is provided to allow the pump tubing to be disconnected from the hub or base of the infusion set when the user wishes to shower, bathe or swim.

There is much focus on occlusions, alarms for occlusions, and design solutions to prevent occlusions in insulin infusion pumps. However, there is no solution to a leading contributor to under-infusion, which is leakage. Leakage at the infusion site may go undetected and lead to serious adverse events. In some situations, the patient may feel wetness, or smell insulin, and thus detect a leak themselves. With some patients, and especially with lower volume infusions, self-detection of leakage may be more difficult or impossible. Undetected leakage can result in serious negative health consequences.

There are products that detect occlusions in the infusion set, but these cannot detect leakage. Accordingly, there is a need for a system to help identify insulin leakage.

A problem with infusion sets and patch pumps occurs when the cannula separates from the skin of the patient or becomes dislodged such that leakage occurs at the infusion site. Infusion pumps generally dispense insulin in small volumes for long periods of time. When leakage occurs, it is often not noticed by the patient for an extended length of time, resulting in an improper dosage.

Accordingly, there is a continuing need in the industry for improved infusion sets and patch pumps that provide adequate leak detection to the patient.

SUMMARY

The present invention is directed to a drug delivery system having a leak detection system. The invention is particularly directed to an insulin infusion device having a leak detector for detecting leaks that occur at an infusion site.

Accordingly, one feature is to provide a fluid delivery device, an insulin delivery device, an infusion set, patch pump or other delivery device having a leak detection component spaced from the cannula or catheter for providing an indication to the patient of leakage at the infusion site.

Another feature of the invention is to provide an insulin delivery device such as an infusion set, patch pump or other delivery device that provides the patient with a visible indicator that leakage has occurred at an infusion site. The visible indicator produces a color change that is visible through at least a portion of the device, component or material that contacts the insulin leaking from the infusion site.

An infusion set or patch pump in an embodiment of the invention includes a cannula for penetrating the skin of a patient for delivering a drug or other pharmaceutical agent. A leak detector is provided to produce a color change by a chemical reaction with one or more compounds in the drug or pharmaceutical agent with a compound on or associated with the leak detector. The leak detector contains chemical compounds that undergo a rapid color change compared to the prior devices when in contact with the drug or pharmaceutical agent. In other embodiments, the leak detector provides a visible indication of contact with the leaking fluid by absorption without necessarily creating color change or chemical reaction with the leaking fluid in the leak detector.

In one embodiment, the leak detector is for an infusion device commonly used for insulin delivery. In an embodiment, the delivery device includes a supply conduit for supplying the substance to the cannula or catheter of the infusion set. The conduit has a first lumen for carrying the substance to the cannula or catheter. A second lumen has an open end at or near the infusion site that contacts and receives the substance that leaks from the infusion site during the introduction of the substance to the patient. The second lumen has a dimension to carry insulin away from the infusion site. Typically the insulin is carried by capillary action to the leak detector that is spaced and/or separate from the hub and cannula or catheter at the infusion site. The leak detector is positioned in a visible location where the fluid is carried away from the infusion site and the cannula or catheter.

The leak detector is positioned in a location spaced from the infusion site to avoid false positive indications from small amounts of insulin that may leak during the insertion of the catheter and/or cannula. During the infusion, an amount of insulin that leaks from the catheter at the infusion site collects around the cannula or catheter. The small dimension of the second lumen of the supply conduit wicks or carries the collected insulin away from the infusion site into contact with the leak detector separate from the hub of the infusion set where a color change occurs that is visible to the patient. The leak detector in this embodiment includes a color changing leak detecting agent.

In one embodiment, a fluid delivery assembly for introducing a fluid to a patient includes a delivery device adapted for delivering a fluid to the patient. The delivery device has a base with a bottom face for attaching to the skin of the patient, and a cannula or catheter extending from said bottom face for penetrating the skin of the patient at an infusion site. A fluid supply conduit has a first lumen connected to the cannula or catheter for supplying the fluid to the cannula or catheter. The fluid contains an active agent and stabilizing agent. The conduit has a second lumen with an open end at the infusion site for capturing leakage of the fluid from the infusion site and carrying the fluid away from the infusion site. The second lumen has a leak detecting agent in an amount to react with the stabilizing agent and produce a visual indication to the patient through at least a portion of the conduit.

In another embodiment, an infusion set includes a base having a cannula or catheter for introducing a substance to a patient at an infusion site and a pump for supplying the substance to the cannula or catheter. A flexible dual-lumen conduit extends between the pump and the cannula or catheter at the infusion site. The conduit has a first lumen for carrying the substance from the pump to the cannula or catheter at the infusion site, and the second lumen. The second lumen has a first end at the infusion site and has a dimension to wick the substance leaking from the infusion site to a color-changing material in said second lumen.

In another embodiment, a method of introducing insulin to a patient and detecting leakage at an infusion site is provided. The method introduces a cannula or catheter of an infusion set into the skin of a patient at an infusion site. The infusion set has a base with a bottom face for attaching to the skin of the patient. The cannula or catheter extends from the bottom face for penetrating the skin of the patient at an infusion site. A fluid supply conduit having a first lumen is connected to the cannula or catheter for supplying the insulin to the cannula or catheter, where the insulin contains a stabilizing agent. The conduit has a second lumen with an open end at the infusion site. Insulin is supplied through the first lumen to the cannula or catheter and introduces the insulin to the patient at the infusion site. The leakage of the insulin at the infusion site is captured and directed away from the infusion site through the second lumen into contact with a leak detecting agent in the second lumen to react with the stabilizing agent insulin and produce a visual indication to the patient through the conduit.

In a further embodiment, an insulin fluid delivery assembly is provided for introducing insulin to a patient. The assembly includes a delivery device adapted for delivering the insulin to the patient. The delivery device has a base with a bottom face for attaching to the skin of the patient, and a cannula extending from the bottom face for penetrating the skin of the patient at an infusion site. The base has a first passage for supplying insulin to the cannula, and a second passage proximate the cannula and having dimension to carry insulin leaking from the infusion site away from the infusion site, where the insulin contains a stabilizing agent. A fluid supply conduit having a lumen is in communication with the first passage of said base for supplying the insulin to the cannula. A second conduit is connected to said second passage for receiving insulin carried through the second passage. The second conduit contains a leak detecting agent positioned for contacting insulin carried through the second passage and second conduit. The leak detecting agent is present in an amount to react with the stabilizing agent and produce a visual indication to the patient through the second conduit.

These and other features of the invention will become apparent from the following drawings and the detailed description of the invention.

BRIEF DESCRIPTION OF THE DRAWINGS

The following is a brief description of the drawings in which.

Throughout the drawings, the reference numbers should be understood to refer the like parts, components, and structures.

DETAILED DESCRIPTION

A solution to the problem of leakage at an infusion site must be affordable to the user, uncomplicated, and designed to align with current usage of pumps and infusion sets. The leak detector of the invention avoids the use of electrical sensors with alarm systems, and devices that are incompatible with currently available insulin pump systems.

Figure 1:
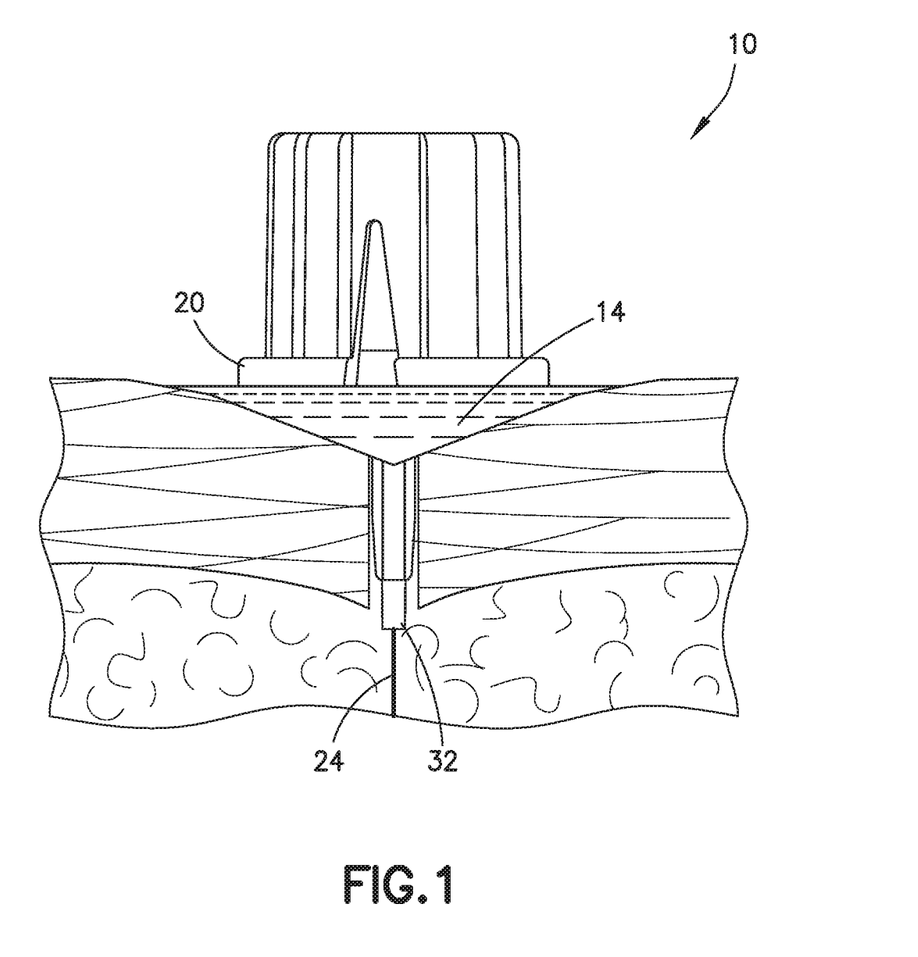
FIG. 1 illustrates an infusion set with the catheter inserted into the patient.
Figure 2:
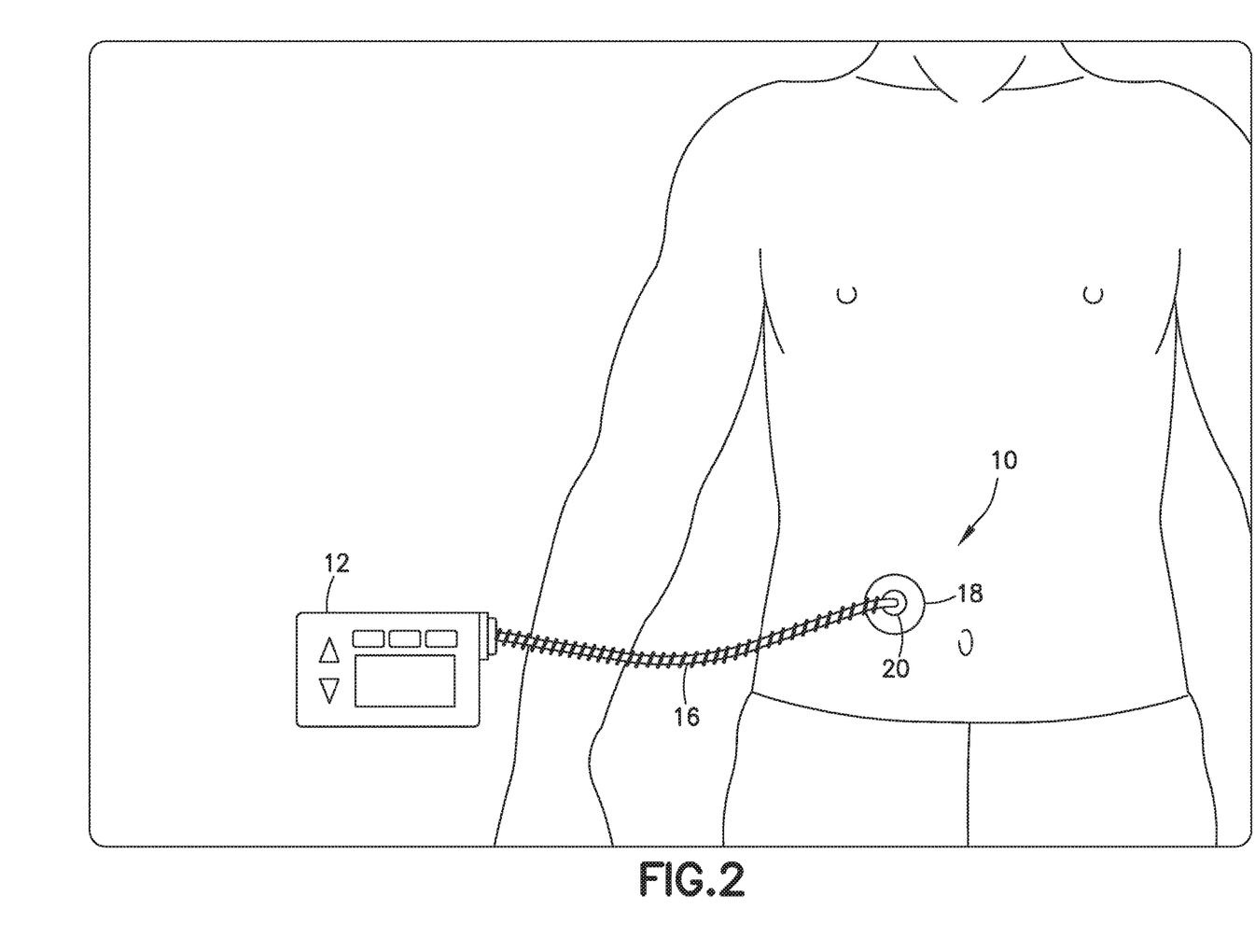
FIG. 2 illustrates the infusion set and pump mechanism during use and attached to the patient.

As illustrated in FIG. 1 and FIG. 2, when a patient uses an infusion set 10 to receive insulin or other medication, it is preferable for all of the insulin to be delivered from the infusion set to the patient. However, it is possible under some circumstances for insulin to leak either from the device, or from the patient, so that at least a portion of the insulin is not delivered to the patient effectively. When this happens, insulin can form a pool 14 under the infusion set, between the infusion set and the skin of the patient, as illustrated in FIG. 1.

Figure 3:
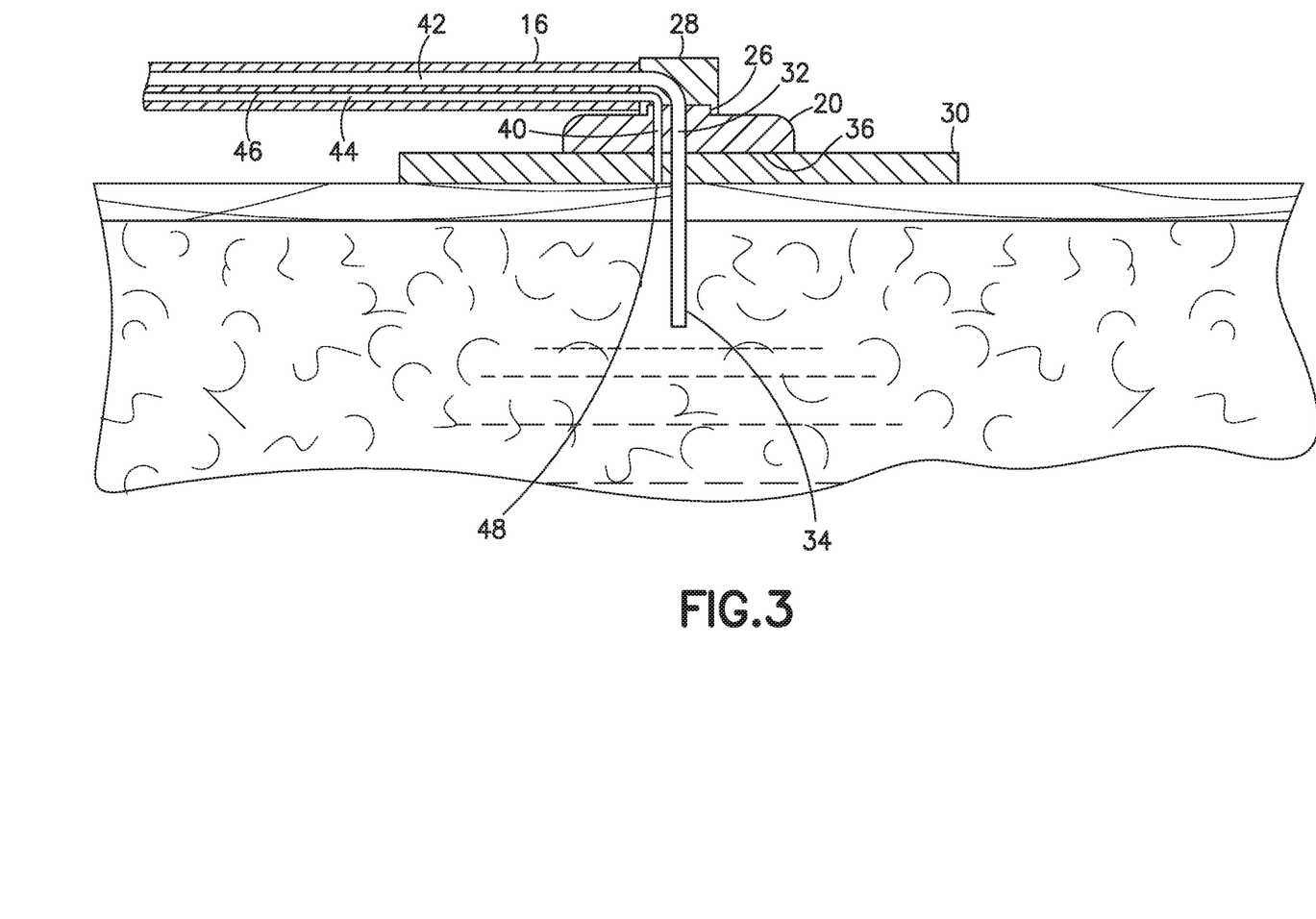
FIG. 3 is a partial cross sectional view of one embodiment of the invention showing the leak detecting agent in the conduit.

The delivery device is typically an infusion set 10 as shown in FIGS. 1 and 2. As shown in FIG. 2, the infusion set 10 includes pump 12 having suitable settings for selecting the infusion rate and time as known in the art. The infusion set 10 has a flexible base 18 and a centrally located hub 20. The base 18 is made of a sufficiently flexible material to conform to the patient's skin when attached. The bottom face of the base 18 includes a pad 30 having an adhesive for attaching the base to the patient as shown in FIG. 3. A protective peel layer is typically provided to cover the adhesive 22 during storage and which is removed by the patient at the time of use. The pad 30 can have a central opening for the cannula 34. In one embodiment, the opening in the pad 30 can be larger than the outer diameter of the cannula 34 so that the open area forms a cavity around the cannula 34 to contain the leaking fluid.

The central hub 20 is attached to the base to provide a substantially fluid-tight seal there between. The central hub 20 has a top face with a fluid port 26 for connecting to a detachable fluid coupling 28 as shown in FIG. 3. The hub 20 is made from a plastic material that can be clear or transparent. The port 26 generally has a substantially cylindrical configuration typically with an outwardly extending annular flange as known in the art for connecting with the conduit coupling 28. The annular flange can connect to a corresponding recess in the coupling 28. A passage 32 extends through the port 26 and hub 20 for supplying the fluid to the patient. A blunt plastic cannula within the fluid connector 28 can penetrate a septum to establish fluid flow to the infusion set.

A cannula 34 or other delivery element for penetrating the skin is coupled to the hub 20 and extends from an interface region on a bottom face 36 of the hub 20 as shown in FIG. 1. The cannula 34 can be a rigid cannula made of stainless steel or a soft flexible cannula as known in the art. The soft flexible cannula typically includes an insertion needle 24 shown in FIG. 1 that is able to penetrate the skin to position the flexible cannula into the skin after which the insertion needle is removed. Typically, the infusion set will have a flexible cannula and an insertion needle as known in the art. As used herein the cannula is intended is intended to refer to a rigid needle, rigid cannula, or a flexible catheter as known in the art.

In the embodiments of the present invention, the use of micro-fluidics and a material that changes appearance or color when wet with insulin, or an indicator within insulin, indicate to the user that a leak has or is occurring at the infusion site. In the area where leakage may occur, an opening is provided to a small channel or lumen that runs along the infusion set conduit or tubing, outside of the infusion fluid supply path. Due to the small size, capillary action will draw the leaked fluid up the conduit lumen or channel away from the infusion set. In one embodiment, the lumen extends the length between the bottom face of the base 18 to a location on a surface of the conduit facing outward toward the patient or other portion of the device that is visible to the patient.

Referring to FIG. 3, the cannula or catheter 34 is inserted into the patient for delivering the substance, such as insulin to the patient. The supply conduit 12 includes a coupling for connecting the hub 20 for providing the fluid connection between the cannula 34 and the fluid supply and pump 12. The pump 16 provides a continuous and controlled supply of the substance to the cannula for delivery to the patient.

A leak detector is a visible indicator providing the patient with a notice or indication of leakage at the infusion site. The leak detector is typically in the form of a color changing leak detecting agent provided on or in the supply conduit 16. The hub 20 as shown in FIG. 3 includes a second passage 40 oriented at or near the cannula or catheter 34. The passage 40 extends from the bottom face 36 of the hub 20 through the hub 20 to the connector or coupling 28 with the supply conduit 16. In the embodiment shown, the hub 20 and the adhesive on the pad 30 do not include a color changing leak detector.

As shown in the embodiment of FIG. 3, the supply conduit 16 has a first lumen or passage 42 for directing the substance from the pump 12 to the cannula or catheter 34 for delivery to the patient. A second lumen 44 in the conduit 16 extends along the longitudinal dimension of the conduit 16. In the embodiment shown in FIG. 3, the passage 40 in the hub 20 connects with the lumen 44 for carrying the substance from the infusion site to the conduit 16. Preferably, the lumen 44 is oriented in a location that is visible to the patient. The passage 40 extends from the bottom face 36 of the hub 20 through the coupling 28. The passage 40 is configured to connect with the lumen 44 to form a continuous passage or lumen for carrying the substance from the infusion site through the lumen.

The second lumen 44 of the conduit 16 has first open end 48 at the bottom face of the hub 20 typically formed by the open end of the passage 40 at or near the cannula or catheter 34 and the infusion site. The substance that leaks from the infusion site collects around the cannula or catheter 34 and contacts the open end 48 of the lumen 44. The lumen 44 has a dimension such that the fluid substance leaking from the infusion site wicks or in drawn up through the passage 40 in the hub away from the infusion site and through the lumen 44 of the conduit 16. In one embodiment, the substance is carried through the lumen 44 by capillary action without the use of pumps or a pressure source. In further embodiments, the lumen 42 and lumen 44 can be formed as separate conduits.

A leak detector 46 is provided to contact the substance carried through the lumen 44 by the capillary action. In one embodiment as shown in FIG. 3, the leak detector 46 is spaced from the cannula or catheter 32 and from the hub 20. In the embodiment shown, the leak detector is separate from the hub 20. The supply conduit 16 is formed from a clear or transparent plastic material so that the substance in the lumen 44 is visible to the patient through the wall of the conduit 16. In the embodiment of FIG. 3, the leak detector 46 is formed on at least part of the inner surface of lumen 44. In one embodiment, the leak detector 46 is formed as coating or layer on the inner surface that is able to contact the substance carried through the lumen 44. The coating can be film of suitable polymer, such as a hydrogel polymer containing a leak detecting agent, which is preferably a color changing leak detecting agent. The entire inner surface of the lumen 44 can be coated with the leak detector 46. In other embodiments, a portion that is less than the entire length of the conduit can be coated or contain the leak detector 46. In one embodiment, the leak detector in the lumen 44 is at or near the coupling 28 in a location that is visible to the patient. The leak detector 46 can cover a portion of the inner surface. Preferably, the leak detector 46 is a coating encircling the entire inner surface of at least a selected portion or section of the conduit 16. In the embodiment shown, the leak detector 46 and the conduit 16 are separate from the from the hub 20.

The color changing leak detector material 46 in the small channel or lumen 44 becomes wet and changes color in contact with the substance, such as from clear to a bright red color indicating an infusion set leak that requires the user's attention. Whenever patients pull out the pump to review any status messages or alerts or to change their clothing, a bright red line on the supply conduit 16 of the infusion set will be easily visible to the patient.

The supply conduit 16 in the embodiment shown is a dual lumen design including two lumens 42, 44 within the flexible tubing of the infusion set. One lumen caries insulin from a pump to the patient and the other lumen is appropriately dimensioned to wick insulin leaking from the infusion site by capillary action away from the leak site. Color changing material 46 may be located within the wicking lumen or at an end of the wicking lumen away from the infusion site. In other embodiments, the color changing leak detector is within the adhesive patch of the infusion set.

Any color may be used as the starting or ending color based on available color-changing materials and what will be most likely to catch user's attention, such as preferably transparent changed to red. The color may either appear or disappear when wet, such as clear to red, or red to clear. The cause of color change may be due to wetness, temperature change, pH change, or any other suitable mechanism, resulting from wetness.

Figure 4:
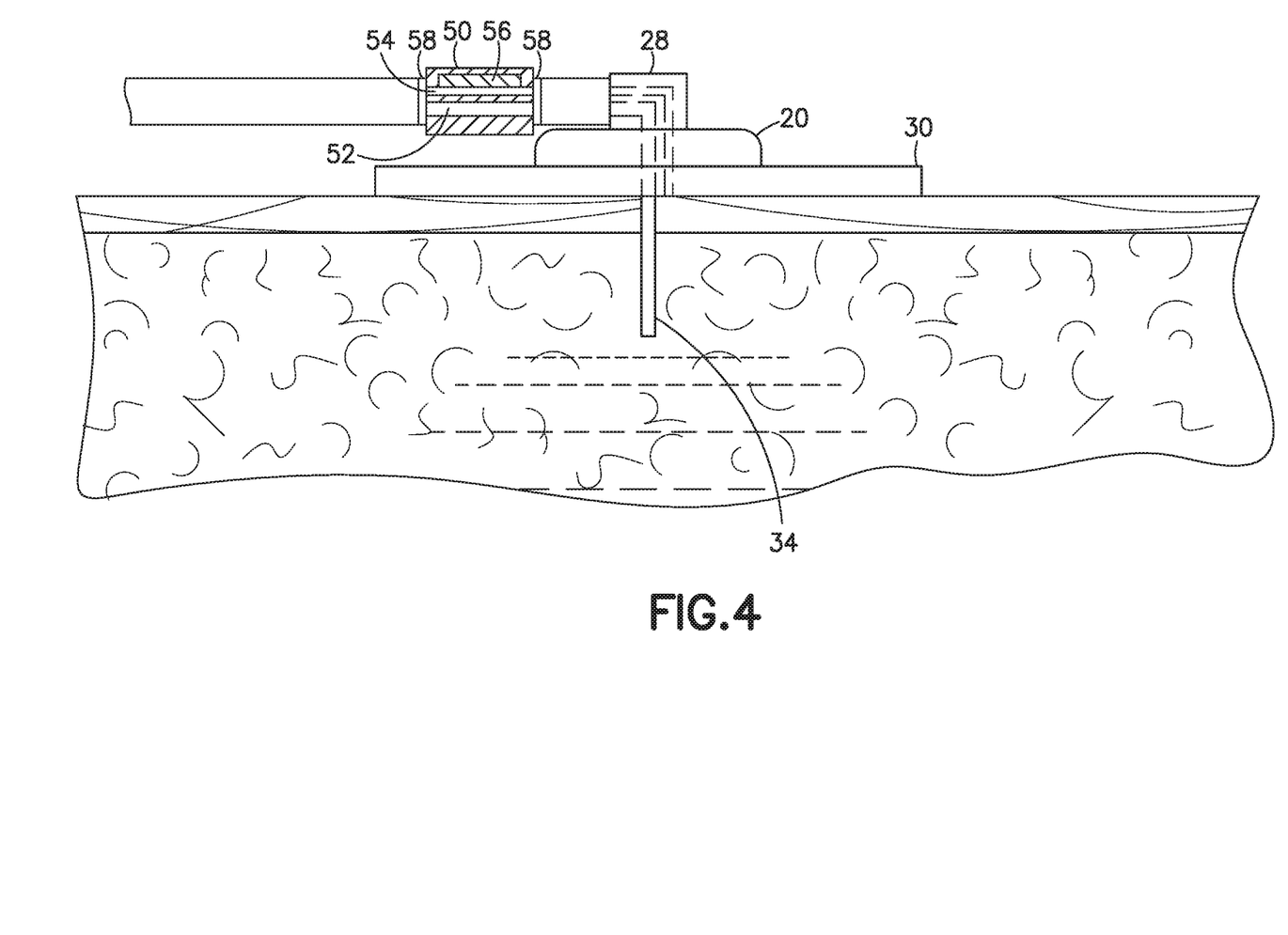
FIG. 4 is a partial cross sectional view of another embodiment of the invention showing the leak detecting agent as a separate unit from the conduit.

In another embodiment shown in FIG. 4, the supply conduit 16 includes a cartridge 50 that can be coupled to and removed from the supply conduit 16 by a suitable coupling 58. As shown in FIG. 4, the cartridge 50 has a first passage 52 connecting with the lumen 42 of conduit 16 and a second passage 54 for connecting with the second lumen 44. In the embodiment shown, the second passage 54 contains a leak detector or indicator 56 that indicates the presence of the leaking substance carried from the leakage at the infusion site. The cartridge 50 is made of clear or transparent plastic material or includes a window providing visualization of the leak detector 56 so that the presence of the substance in the cartridge is readily visible to the patient. The leak detector 56 absorbs at least a portion of the substance to wet the indicator where the wet detector 56 is visible through the wall of the cartridge 50 or a window in the cartridge. The leak detector can be an absorbent material, such as a hydrogel or porous fiber pad that is able provide a visible indicator when contacted by the substance.

In another embodiment the leak detector 46 can be a separate unit that communicates with the lumen 44 through port or coupling. Alternatively, a separate conduit can connected to the passage 40 of the hub to carry the insulin to a separate device or cartridge containing a leak detector that is not part of the supply conduit.

In one embodiment, the leak detector 56 is an absorbent material containing a color changing reactive compound that reacts with substance carried through the lumen 44. In an embodiment, the reactive compound is reactive with one or more compounds in the substance.

The leak detectors 46 and 56 in the embodiments of the infusion set includes a color-changing leak detecting agent. The leak detecting agent is a compound that is able to provide a visual color indicator when the leaking fluid contacts the leak detector in the event of leakage at the infusion site. The color-changing compound of the leak detector can applied as a coating on a suitable surface of the device that contacts the fluid or on a suitable support, such as an absorbent material. The leak detector and the color change is visible by the user through the transparent portions of the device. As shown in FIG. 3, the infusion site at the cannula penetration site typically is where leakage occurs. The leakage can be the result of an improperly inserted cannula or a cannula that has been partially or completely removed by movement of the infusion set 10. In preferred embodiments of the invention, the leak detector is positioned to provide a rapid visual indicator in a conspicuous location to the patient that leakage has occurred, thereby providing an opportunity to correct the leakage and provide the intended dosage. The leak detector provides a visual color indicator of leakage through a portion or component of the delivery device.

In an embodiment of the device, the leak detector can be a transparent high diffusion hydrogel having at least one compound dispersed therein that is capable of undergoing a color change when contacted with the infusion liquid. The hydrogel is preferably a film or a shaped member for attaching the hydrogel to one or more surfaces of the infusion set, such as an inner surface of the conduit 16. Examples of hydrogels include polyacrylamides, silicone hydrogels, crosslinked polyethylene oxide and crosslinked polyvinylpyrrolidone. The clear or transparent components of the infusion set enable visualization of the reaction by a color change through one or more parts of the infusion set.

In one embodiment of the invention, the infusion liquid is an insulin formulation. The leak detector contains at least one component that reacts with a component or compound of the insulin formulation that is not present in body fluids to avoid giving a false indication of leakage of the insulin formulation. Insulin formulations typically include insulin, hexamer zinc stabilizer preservatives, pH buffers, surfactants such as glycerol and tonicity agents such as NaCl. Common insulin preservatives or stabilizing agents include m-cresol, phenol, and mixtures thereof.

In one preferred embodiment of the invention, the leak detector 46 and 56 includes one or more compounds that react with the stabilizing agents, namely m-cresol and/or phenol, to produce a visual color change when the infusion liquid contacts the leak detector. The color changing compounds in the leak detector can be clear or opaque initially and produce a color change when reacted with the stabilizing agents of the insulin or other infusion liquid.

The color changing compounds of an embodiment of the invention include a mixture of 4-aminoantipyrine and an oxidizing agent in an effective amount to produce a color change by reacting with the stabilizing agents when the infusion liquid contacts the leak detector 46 and 56. A suitable oxidizing agent is potassium persulfate, $K_2S_2O_8$ or potassium ferricyanide. The mixture of 4-aminoantipyrine and potassium persulfate reacts with the m-cresol and/or phenol in the insulin formulation to transform the leak detector from a clear hydrogel to a dark blue color that is visible through the transparent conduit 16 or the cartridge 50. Potassium persulfate is an oxidizing agent and has been found to provide a rapid color change in the presence of phenol, m-cresol and 4-aminoantipyrine compared to other oxidizing agents. For example, it has been found that potassium persulfate provides a faster color change compared to potassium ferricyanide. The m-cresol and/or phenol react with potassium persulfate and 4-aminoantipyrine to produce quinoneimine having a dark blue color that is visible through the device.

In further embodiments, the hydrogel film or absorbent material can also include a catalyst or enzyme to enhance the speed of the reaction and amplify the color change. In one embodiment, horseradish peroxidase (HRP) is included in the hydrogel matrix or absorbent material in combination with the 4-aminoantipyrine and potassium persulfate. A deep blue complex is formed during the reaction with m-cresol and phenol. Horseradish peroxidase functions as a catalyst to create an enzymatic amplification of the reaction and the blue complex formed by the reaction. The presence of the horseradish peroxidase enables rapid detection of small amounts of insulin to enable patients to observe the leakage reliably and quickly after the leakage starts.

The above description of the embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A fluid delivery device for introducing a fluid to a patient, comprising;
   a delivery device adapted for delivering a fluid to the patient, the delivery device having a base with a bottom face for attaching to the skin of the patient, and a cannula extending from said bottom face for penetrating the skin of the patient at an infusion site; and
   a fluid supply conduit having a first lumen connected to said cannula for supplying the fluid to the cannula, where the fluid contains an active agent and stabilizing agent, the conduit having a second lumen with an open end at the infusion site for capturing leakage of the fluid from the infusion site and carry the fluid away from the infusion site, and where said second lumen has a leak detecting agent in an amount to react with the stabilizing agent and produce a visual indication to the patient through the conduit.

2. The fluid delivery device of claim 1, wherein said base has a coupling member, and said fluid supply conduit has a coupling member for coupling to said base, said base having a passage extending between said bottom face at the infusion site through said coupling and said conduit, said passage having a dimension to carry fluid at the infusion site to the second lumen of the fluid supply conduit by capillary action.

3. The fluid delivery device of claim 2, wherein a least a portion of inner surface of the second lumen contains the leak detecting agent.

4. The fluid delivery device of claim 1, wherein said second lumen has a dimension to carry the fluid by capillary action to the leak detecting agent.

5. The fluid delivery device of claim 4, wherein said supply conduit has a transparent portion for visualizing the indicator produced by the leak detecting agent in the second lumen.

6. The fluid delivery device of claim 1, wherein said supply conduit includes a removable cartridge positioned in the flow path of said conduit, and where said cartridge has first passage for supplying said fluid to the cannula, and a second passage connected to said second lumen of said conduit for receiving said fluid leaking from said infusion site, said second passage of said cartridge containing said leak detecting agent.

7. The fluid delivery device of claim 1, wherein said fluid is insulin and where said stabilizing agent is selected from the group consisting of phenol, cresol and mixtures thereof, and where said leak indicator is 4-amino-antipyrine and an oxidizing agent.

8. An infusion set comprising;
a base having a cannula for introducing a substance to a patient at an infusion site;
a pump for supplying the substance to the cannula; and
a flexible dual-lumen conduit extending between said pump device and said cannula at the infusion site, the conduit having a first lumen for carrying the substance from the pump to the cannula at the infusion site, and the second lumen having a first end at the infusion site and being dimensioned to wick the substance leaking from the infusion site away from the infusion site to a leak detector containing a color-changing leak detecting agent in said second lumen.

9. The infusion set of claim 8, wherein the color changing leak detecting agent is within the second lumen.

10. The infusion set of claim 8, wherein the color changing leak detecting agent is located at a second end of the second lumen.

11. The infusion set of claim 8, wherein a least a portion of inner surface of the second lumen contains the color changing leak detecting agent.

12. The infusion set of claim 8, wherein said second lumen has a dimension to carry the fluid by capillary action to the color changing leak detecting agent.

13. The infusion set of claim 12, wherein said supply conduit has a transparent portion for visualizing the indicator produced by the color changing leak detecting agent in the second lumen.

14. The infusion set of claim 8, wherein said supply conduit includes a removable cartridge positioned in the flow path of said conduit, and where said cartridge has first passage for supplying said fluid to the cannula, and a second passage connected to said second lumen of said conduit for receiving said fluid leaking from said infusion site, said second passage of said cartridge containing said color changing leak detecting agent.

15. The fluid delivery device of claim 8, wherein said fluid is insulin and where said stabilizing agent is selected from the group consisting of phenol, cresol and mixtures thereof, and where said leak indicator is 4-amino-antipyrine and an oxidizing agent.

16. A method of introducing insulin to a patient and detecting leakage at an infusion site, said method comprising the steps of:
introducing a cannula of an infusion set into the skin of a patient at an infusion site, said infusion set having a base with a base with a bottom face for attaching to the skin of the patient, said cannula extending from said bottom face for penetrating the skin of the patient at an infusion site; and a fluid supply conduit having a first lumen connected to said cannula for supplying the insulin to the cannula, where the insulin contains a stabilizing agent, the conduit having a second lumen with an open end at the infusion site;
supplying insulin through said first lumen to said cannula and introducing said insulin to the patient at the infusion site; and
capturing leakage of the insulin at the infusion site and directing the leakage of insulin through said second lumen into contact with a leak detecting agent in said second lumen to react with the stabilizing agent insulin and produce a visual indication to the patient through the conduit.

17. The method of claim 16, wherein a least a portion of inner surface of the second lumen contains the leak detecting agent.

18. The method of claim 17, wherein said second lumen has a dimension to carry the insulin by capillary action to the leak detecting agent.

19. The method of claim 18, wherein said supply conduit has a transparent portion for visualizing the indicator produced by the leak detecting agent in the second lumen.

20. The method of claim 16, wherein said supply conduit includes a removable cartridge positioned in the flow path of said conduit, and where said cartridge has first passage for supplying said fluid to the cannula, and a second passage connected to said second lumen of said conduit for receiving said fluid leaking from said infusion site, said second passage of said cartridge containing said leak detecting agent.

21. The method of claim 16, wherein said stabilizing agent is selected from the group consisting of phenol, cresol and mixtures thereof, and where said leak detecting agent is 4-amino-antipyrine and an oxidizing agent.

22. An insulin fluid delivery assembly for introducing insulin to a patient, comprising;
a delivery device adapted for delivering the insulin to the patient, the delivery device having a base with a bottom face for attaching to the skin of the patient, and a cannula extending from said bottom face for penetrating the skin of the patient at an infusion site, said base having a first passage for supplying insulin to said cannula, and a second passage proximate said cannula and having dimension to carry insulin leaking from the infusion site away from the infusion site, and where the insulin contains a stabilizing agent; and
a fluid supply conduit having a lumen communicating with said first passage of said base for supplying the insulin to the cannula; and
a second conduit connected to said second passage for receiving insulin carried through said second passage, said second conduit containing a leak detecting agent positioned for contacting insulin carried through said second passage and second conduit, and where said has a leak detecting agent is present in an amount to react with the stabilizing agent and produce a visual indication to the patient through the second conduit.

* * * * *